United States Patent
Lee et al.

(10) Patent No.: US 6,613,458 B2
(45) Date of Patent: Sep. 2, 2003

(54) ORGANIC ELECTROLUMINESCENT ELEMENTS

(75) Inventors: Shuit-Tong Lee, Kowloon (HK); Chun-Sing Lee, Kowloon (HK); Liang-Sun Hung, Kowloon (HK); Bao-Xiu Mi, Kowloon (HK); Zhi-Qiang Gao, Kowloon (HK)

(73) Assignee: CityU Research Ltd., Kowloon Tong (HK)

( * ) Notice: Subject to any disclaimer, the term of this patent is extended or adjusted under 35 U.S.C. 154(b) by 22 days.

(21) Appl. No.: 09/952,215

(22) Filed: Sep. 13, 2001

(65) Prior Publication Data

US 2003/0082403 A1 May 1, 2003

(51) Int. Cl.$^7$ ............................................. H05B 33/14
(52) U.S. Cl. ...................... 428/690; 428/917; 313/502; 313/504; 313/506; 252/301.16; 257/101
(58) Field of Search .......................... 257/101; 428/690, 428/917; 313/502, 504, 506; 252/301.16

(56) References Cited

U.S. PATENT DOCUMENTS 5,739,545 A * 4/1998 Guha et al. .................. 257/40
6,259,202 B1 * 7/2001 Sturm et al. ................ 313/504

OTHER PUBLICATIONS

"Efficient green electroluminescence of pure chromaticity from a polycyclic aromatic hydrocarbon", Mi et al., Journal of Materials Chemistry, 2001, vol. 11, pp. 2244–2247.*

Sano et al., "Organic electroluminescent devices doped with condensed polycyclic aromatic compounds," *Synthetic Metals*, vol. 91, pp. 27–30 (1997).

Buhler, "Reaction of Lithium Alkyls with Aldehydes and Ketones," *J. Org. Chem.*, vol. 38, No. 5, pp. 904–906 (1973).

Clar et al., "Aromatic Hydrocarbons," *J. Amer. Chem. Soc.*, vol. 75, pp. 1108–1111 (1953).

* cited by examiner

Primary Examiner—Cynthia H. Kelly
Assistant Examiner—Dawn Garrett
(74) Attorney, Agent, or Firm—Merchant & Gould P.C.

(57) ABSTRACT

An electroluminescent element has an anode, a cathode, and an organic layer structure between the two electrodes. The layer structure has a luminescent zone containing 1,9-perinaphtylene-10-1'-naphthylanthracene or derivatives as dopant. The luminescent material utilized as dopant has the following structure called pNNA or pNNA derivatives:

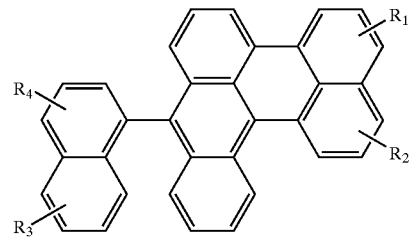

Wherein:

$R_1$, $R_2$, $R_3$, $R_4$ are individual substituents or a group of substituents, and they may be identical or different. Each substituent is individually selected from the following groups consisting of:

H, alkyl (—R), halogen (—X), aryl (—Ar), alkenyl (RCH=CH—), allyl(CH$_2$=CHCH$_2$—), cyano (NC—), isocyano (CN—), amino (H$_2$N—), tertiary amino (R$_2$N—or Ar$_1$Ar$_2$N—), amide (RCONR—), nitro (N$_2$O—), acyl (RCO—), carboxyl (—CO$_2$H), alkoxyl (RO—), alkylsulfonyl (RSO$_2$—), hydroxy (HO—) and single or fused aromatic heterocyclic rings.

12 Claims, 2 Drawing Sheets

ORGANIC ELECTROLUMINESCENT ELEMENTS

FIELD OF THE INVENTION

The present invention relates to organic electroluminescent (EL) elements. More specifically, the invention relates to the use of a novel class of organic material for producing efficient organic EL devices.

BACKGROUND OF THE INVENTION

Nowadays, with the fast development of science and technology, and their wide application to daily life, the requirement for good interfaces between users and machines is growing, such as information display for instruments, televisions, computers and so on. In order to gain ample, correct, concise, and high-speed information from the machine, the display elements have been widely studied.

While cathode ray tubes (CRTs) clearly dominate the market with their bright, saturated colors, they are also known to be heavy, power consuming, and bulky. For these reasons, flat panel displays are a highly attractive alternative for computers, television, wall-mounted large-screen video displays and a wide range of other applications.

An example of the flat panel display is the active-matrix liquid-crystal display, which is commercially available. Even though this technology is now widely used for laptop computer displays, in general it is not considered to be a widespread replacement for the CRT technology. The major shortcomings of the LCD-based display are that it is an inefficient color subtractive technology, requiring a power consumptive backlight. Also, it is relatively slow, and has a narrow viewing angle. One alternative to LCDs is based on conventional semiconductor light-emitting diode (LED) technology. However, the very high costs associated with the requirement of epitaxial multilayer structures make them an unlikely choice for use in low-cost displays in the near future.

A promising flat panel display free from the above-mentioned disadvantages is based on organic light-emitting diodes (OLEDs) that use an organic luminescent material for light emission. The organic luminescent materials are very attractive due to their versatility, richness in blue photoluminescence, and high photo-luminescent quantum yields.

The advantages of the OLED display are self-luminous, capable of high-speed response, and independent on viewing angle. These advantages will no doubt be successfully exploited, and the commercial use for organic EL devices will be realized in the near future.

To obtain high-performance OELDs with low carrier injection barriers, high electroluminescence (EL) efficiency and long lifetime, materials design and device configurations are two important factors. It is desirable that the OELD materials possess the following properties: good carrier transport properties, high photoluminescence (PL) quantum yield, and suitable ionization potential (IP) and/or electron affinity (EA). Thus, the synthesis of highly fluorescent and stable materials that can be utilized in OELDs is one of the most challenging works in this field.

Some polycyclic aromatic hydrocarbons (PAHs) have very high PL quantum yield and thus have been used in OELDs. Here are some reported examples using this kind of materials in OLEDs: 1) T. Sano, H. Fujii, Y. Nishio, Y. Hamada, H. Takahashi, K. Shibata, Syn. Met., 91, 27(1997); 2) J. Shi, C. W. Tang, C. H. Chen, U.S. Pat. No. 593,572 (1999); and 3) S. Tamura; T. Ishibashi, U.S. Pat. No. 5,858,564. The pure hydrocarbon conjugated structure of the compounds intrinsically determines their relatively high carrier transport abilities. Meanwhile, most of them are highly luminescent and relatively stable. It is thus considered that the PAHs compounds may have special importance for OELD applications.

In our invention, we have synthesized a new PAH compound, 1,9-perinaphthylene-10-1'-naphthylanthracene (pNNA), and utilized this compound in OLED fabrication.

SUMMARY OF THE INVENTION

The present invention provides an organic EL element comprising an anode, a cathode, and an organic light-emitting structure between the anode and the cathode. The luminescent material disclosed in this invention is utilized as a dopant in the organic light-emitting structure and has the following structure called pNNA or pNNA derivatives:

Wherein:
$R_1$, $R_2$, $R_3$, $R_4$ are individual substituents or a group of substituents, and they may be identical or different. Each substituent is individually selected from the following groups consisting of:
H, alkyl (—R), halogen (—X), aryl (—Ar), alkenyl (RCH=CH—), allyl ($CH_2$=$CHCH_2$—), cyano (NC—), isocyano (CN—), amino ($H_2N$—), tertiary amino ($R_2N$— or $Ar_1Ar_2N$—), amide (RCONR—), nitro ($N_2O$—), acyl (RCO—), carboxyl (—$CO_2H$), alkoxyl (RO—), alkylsulfonyl ($RSO_2$—), hydroxy (HO—) and single or fused aromatic heterocyclic rings.

The electroluminescent element of the present invention emits light from pNNA or pNNA derivatives.

The first aspect of the present invention resides in an electroluminescent element having an anode, a cathode, and an organic layer structure between the two electrodes. The organic layer structure has a luminescent zone containing pNNA or one of its derivatives as a dopant. The second aspect of the present invention resides in a luminescent display formed of such electroluminescent elements.

The advantage of this invention is that because the pNNA or its derivatives are highly efficient with a narrow emission peak and a stable conjugated system, OLEDs utilizing these materials as a dopant exhibit high power efficiency, color purity and stability

BRIEF DESCRIPTION OF THE DRAWINGS

These and other advantages of this invention can be better appreciated by referring to the following detailed description of examples of the invention in conjunction with the drawing in which.

DETAILED DESCRIPTION OF THE PREFFERRED EMBODIMENTS

Figure 1:
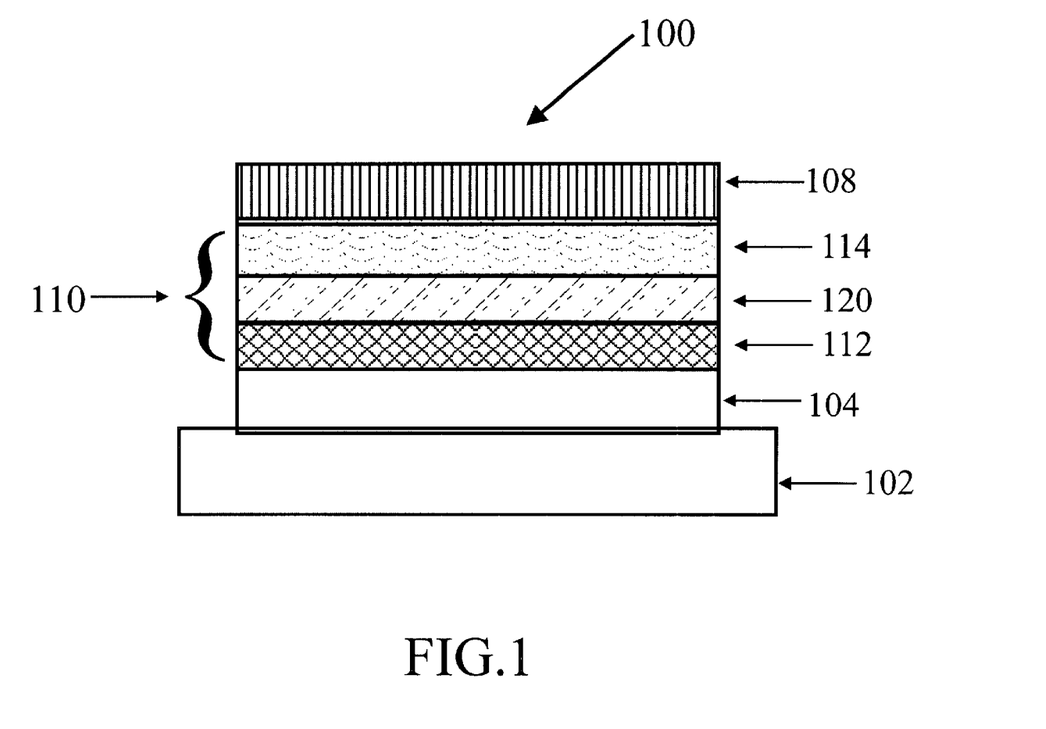
FIG. 1. A schematic diagram of an embodiment of the organic LEDs in accordance with the present invention.
Figure 2:
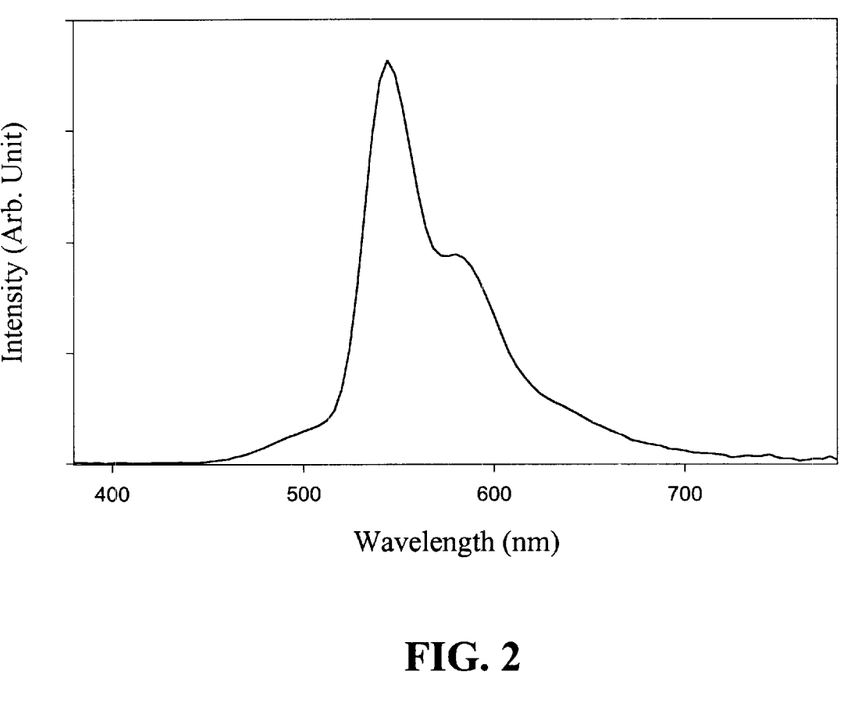
FIG. 2. A emission spectrum of the organic LEDs prepared in Example 5.

Referring to the FIG. 1, an organic EL device 100 is shown. It has, in order, a transparent substrate 102, a bottom electrode layer 104, an organic layer structure 110, and a top electrode layer 108.

Substrate 102 is a transparent glass, and bottom electrode 104 is a transparent and conductive layer having a high-work function greater than 4.1 eV. The materials are selected from the group of a metal oxide, gallium nitride, zinc selenide, and zinc sulphide. The metal oxide includes indium tin oxide, magnesium indium oxide, fluorine tin oxide, nickel tungsten oxide, cadmium tin oxide and aluminium zinc oxide etc. In some applications substrate 102 is opaque and formed of a ceramic material or a semiconductor. In such a case bottom electrode 104 is selected from a metal or metal alloy having a work-function greater than 4.1 eV. The metals include gold, iridium, palladium, and platinum.

Organic layer structure 110 in FIG. 1 consists of a hole transport layer (HTL) 112, an emissive layer (EL) 120, and an electron transport layer (ETL) 114.

Representative materials of HTL 112 are diamine derivatives (compound 1–4) with the thickness selected in the range of 30 nm to 200 nm. ETL 114 is formed of metal chelated oxinoid compounds, and compound 5) is one of them. The practical thickness of ETL is 30 nm to 150 nm.

Compound 1

Compound 2

Compound 3

Compound 4

Compound 5

Top electrode layer 108 is a metal or metal alloy electrode with a work function less than 4 eV, such as Mg:Ag, Li:AL, Mg:In etc, acting as an electron injector. The electron injector is about 50–300 nm thick, and can be deposited by thermal evaporation.

EL is formed by doping pNNA or a derivative in the electron transport material (114) or in the hole transport material (112).The emissive layer (EL 120) where light is emitted in response to electron-hole recombination contains pNNA or a derivative of the following formula:

Wherein:
$R_1$, $R_2$, $R_3$, $R_4$ are individual substituents or a group of substituents, and they may be identical or different.

Each substituent is individually selected from the following groups consisting of:

H, alkyl (—R), halogen (—X), aryl (—Ar), alkenyl (RCH=CH—), allyl (CH$_2$=CHCH$_2$—), cyano (NC—), isocyano (CN—), amino (H$_2$N—), tertiary amino (R$_2$N— or Ar$_1$Ar$_2$N—), amide (RCONR—), nitro (N$_2$O—), acyl (RCO—), carboxyl (—CO$_2$H), alkoxyl (RO—), alkylsulfonyl (RSO$_2$—), hydroxy (HO—) and single or fused aromatic heterocyclic rings;

Compounds listed in number 6 to 35 are typical examples of the present invention, while it is understood that the present invention shall not be limited to these compounds.

Compound 6

Compound 7

Compound 8

Compound 9

Compound 10

Compound 11

Compound 12

Compound 13

-continued

Compound 14

Compound 15

Compound 16

Compound 17

Compound 18

Compound 19

Compound 20

-continued

Compound 21

Compound 22

Compound 23

Compound 24

Compound 25

Compound 26

Compound 27

Compound 28

-continued

Compound 29

Compound 30

Compound 31

Compound 32

Compound 33

Compound 34

Compound 35

In the above example, compound 6 is represented as pNNA; while compound 7 to compound 17 belong to the alkyl derivative of pNNA; Compound 18 to compound 19 are of the type of halogen derivatives of pNNA; Compound 20 to compound 22 belong to the aryl derivative of pNNA; Compound 23, compound 24, compound 25, and compound 26 belong to alkenyl, allyl, cyano, and isocyano derivative of pNNA respectively; Compound 27 to 34 belong to the tertiary amino derivative of pNNA; Compound 35 belongs to the alkoxyl derivative of pNNA. Obviously, all these compounds contain the pNNA back bone. They are similar in optical transition processes, although the substitution groups may have some influences on their emission performance, such as a small red shift or blue shift in emission peaks. However, all these materials are good emitting materials that can be used in OLED fabrication.

The organic EL elements of the present invention have applications in monochrome display and multi-color display. They can also be used as a lightening source or for any other optical applications.

The invention and its advantages are further illustrated by the specific examples as follows:

EXAMPLES

More detailed description of examples of the invention will be given in the following examples, which are not intended to restrict the scope of the invention.

The organic EL element 100 of double-hetero structure in FIG. 1 utilizes the luminescent material pNNA or a derivative thereof represented by the following formula:

Wherein:

$R_1$, $R_2$, $R_3$, $R_4$ are individual substituents or a group of substituents, and they may be identical or different. Each substituent is individually selected from the following groups consisting of:

H, alkyl (—R), halogen (—X), aryl (—Ar), alkenyl (RCH=CH—), allyl(CH$_2$=CHCH$_2$—), cyano (NC—), isocyano (CN—), amino (H$_2$N—), tertiary amino (R$_2$N— or Ar$_1$Ar$_2$N—), amide (RCONR—), nitro (N$_2$O—), acyl (RCO—), carboxyl (—CO$_2$H), alkoxyl (RO—), alkylsulfonyl (RSO$_2$—), hydroxy (HO—) and single or fused aromatic heterocyclic rings;

The pNNA or a derivative thereof used in this invention application can be synthesized by the process reported by E. CLAR, W. KELLY, AND (IN PART) J. W. WRIGHT in J. Chem. Soc., 1108(1954), as shown in the following scheme.

The first step reaction also can be done by lithium reaction reported by JERRY D. BUHLER in J. Org. Chem., V38, 904(1973)

Example 1

Synthesis of 1-chloro-9,10-dihydro-9,10-di-1'-naphthylanthracene Using Grignard Reagent A suspension of 1-chloroanthraquinone 3.06 g (12.6 mmol) in dry tetrahydrofuran (THF) 60 ml was added with stirring to 1-naphthylmagnesium bromide prepared from 1-bromonaphthalene (7 ml, 50 mml) and magnesium turning 1.2 g (49.4 mmol) in THF 20 ml. The mixture was heated to reflux under nitrogen for 3 hours with continuous stirring. The thick suspension was decomposed by pouring it into dilute acetic acid containing ice. Then steam distilled the solvent, getting out THF and some naphthalene. The product was triturated and washed with ether 40 ml, digested thoroughly with a large excess of alkaline sodium dithionite solution to remove unchanged starting material, and washed with hot water, then dried to get crude product. Crystallisation from 1,2,4-trichlorobenzene gave white color pure product can be obtained.

Example 2

Synthesis of 1-chloro-9,10-dihydro-9,10-di-1'-naphthylanthracene Using Lithium Reagent Place 2.6 g (12.4mmol) of 1-bromonaphthalene in a two-necked, 100 ml round bottomed flask containing a magnetic bar. Fit a rubber septum to one of the necks of the flask and connect the other neck to vacuum-nitrogen line. Evacuate the flask and purge nitrogen to it alternatively for three time. Maintain a static atmosphere of nitrogen in the flask throughout the reaction by passing a low stream of nitrogen through the nitrogen line. Cool the flask in an acetone ice bath and transfer 15 ml dry tetrahydrofuran (THF) to the flask via the septum using a syringe. Stir the cooled (−78° C.) suspension and add 8.9 ml (14.2 mmol) of n-BuLi (1.6 M in hexane) via a syringe. Stir the flask solution at −78° C. for 1 hour, and then add a suspension of 1-chloro-anthraquinone 1.5 g (6.2 mmol) in dry THF (25 ml). Stir the reaction mixture under −78° C. for another 1 hour. Then allowed to warm up to room temperature. Add 30 ml 2M $Na_2CO_3$ to hydrolyze the reaction mixture and stirred for another 0.5 hours. Filtered, washed with water, ether, and THF, obtaining yellow product used directly to the second step reaction.

Example 3

Synthesis of 1-chloro-9,10-di-1'-naphthylanthracene

A suspension of the 1-chloro-9,10-dihydro-9,10-di-1'-naphthylanthracene 1.4 g in acetic acid 8.5 ml and hydriodic acid 1.2 ml was heated under reflux for 15 min, cooled filtered, and washed with acetic acid and benzene, to give a yellow product, which crystallised from 1,2,4-trichlorobenzene to get pure product.

Example 4

Synthesis of 1,9-perinaphthylene-10-1'-naphthylanthracene

A mixture of 1-chloro-9,10-di-1'-naphthylanthracene 1.2 g, powdered potassium hydroxide 6 g, and quinoline 8 ml was heated under reflux for 45 min. The reaction color changed through red to brown and to dark brown. The quinoline layer was decanted into diluted hydrochloric acid, getting dark brown precipitate. After washed with hydrochloric acid and water, and dried, use column to obtain red pure product.

Example 5

This example illustrates an organic EL device 100 (FIG. 1) in which the compound 6 was doped into the electron-transport material to form EL 120.

The ITO glass substrate (102 plus 104) was cleaned with detergent and deionized water and dried in an oven for about two hours. Then it was treated with UV-Ozone for 25 minutes before loading into a deposition chamber. The organic films of hole-transport layer (112), N,N'-bis-(1-naphthyl)-N,N'-diphenylbenzidine (NPB) (700 Angstroms), was deposited by using a tantalum boat. Then, a light-emitting layer 120 of doped 1,9-perinaphthylene-10-1'-naphthylanthracene (compound 6) in ALQ (tris(8-hydroxy-quinolinato)aluminum(III)) (350 Angstroms) was sequentially deposited onto the hole transporting layer 112. The concentration of the dopant compound 6 in ALQ is 2% (in weight). An electron-transport layer 114 of ALQ (350 Angstroms) was then deposited onto the light-emitting layer 120. Finally, a cathode 108 (2000 Angstroms) was deposited on the top of layer 114, which comprised of 10:1 Mg and Ag.

The device at 7.9 volts exhibited a current density of 20 $mA/cm^2$ and an electroluminescence efficiency of 3.8 Cd/A. The color was green and peaked at 545 nm with a shoulder at 583 nm.

Example 6

This example illustrates an organic EL device 100 (FIG. 1) in which the pNNA compound was doped into the hole-transport material to form EL 120.

The ITO glass substrate (102 plus 104) was cleaned with detergent and deionized water and dried in an oven for about two hours. Then it was treated with UV-Ozone for 25 minutes before loading into a deposition chamber. The organic films of hole-transport layer (112), N,N'-bis-(1-naphthyl)-N,N'-diphenylbenzidine (NPB) (350 Angstroms), was deposited by using a tantalum boat. Then, a light-emitting layer 120 of doped 1,9-perinaphthylene-10-1'-naphthylanthracene (compound 6) in NPB (350 Angstroms) was sequentially deposited onto the hole-transporting layer 112. The concentration of the dopant compound6 in NPB is 5% (in weight). An electron-transport layer 114 of ALQ (tris(8-hydroxy-quinolinato)aluminum(III)) (700 Angstroms) was then deposited onto the light-emitting layer 120. Finally, a cathode 108 (2000 Angstroms) was deposited on the top of layer 114, which comprised of 10:1 Mg and Ag.

The device at 9.0 volts exhibited a current density of 20 $mA/cm^2$ and an electroluminescence efficiency of 1.2 cd/A. The color was green and peaked at 547 nm with a shoulder at 583 nm.

Example 7

This example illustrates an organic EL device 100 (FIG. 1) in which the pNNA compound was mixed with electron transport material with a ratio of 1:400 to form EL 120.

The ITO glass substrate (102 plus 104) was cleaned with detergent and deionized water and dried in an oven for about two hours. Then it was treated with UV-Ozone for 25 minutes before loading into a deposition chamber. The organic films of hole-transport layer (112), N,N'-bis-(1-naphthyl)-N,N'-diphenylbenzidine (NPB) (700 Angstroms), was deposited by using a tantalum boat. Then, a light-emitting layer 120 of a mixture containing 1,9-perinaphthylene-10-1'-naphthylanthracene (compound 6) and ALQ (tris(8-hydroxy-quinolinato)aluminum(III)) in a weight ratio of 1:400 (350 Angstroms) was sequentially deposited onto the hole-transporting layer 112. An electron-transport layer 114 of ALQ (350 Angstroms) was then deposited onto the light-emitting layer 120. Finally, a cathode 108 (2000 Angstroms) was deposited on the top of layer 114, which comprised of 10:1 Mg and Ag.

The device at 8.4 volts exhibited a current density of 20 mA/cm² and an electroluminescence efficiency of 5.2 cd/A. The color was green and peaked at 544 nm with a shoulder at 580 nm.

Example 8

This example illustrates an organic EL device 100 (FIG. 1) in which the pNNA compound was mixed with electron transport material with a ratio of 1:800 to form EL 120.

The ITO glass substrate (102 plus 104) was cleaned with detergent and deionized water and dried in an oven for about two hours. Then it was treated with UV-Ozone for 25 minutes before loading into a deposition chamber. The organic film of hole-transport layer (112), N,N'-bis-(1-naphthyl)-N,N'-diphenylbenzidine (NPB) (700 Angstroms), was deposited by using a tantalum boat. Then, a light-emitting layer 120 of a mixture containing 1,9-perinaphthylene-10-1'-naphthylanthracene (compound 6) and ALQ (tris(8-hydroxy-quinolinato)aluminum(III)) in a weight ratio of 1:800 (350 Angstroms) was sequentially deposited onto the hole-transporting layer 112. An electron-transport layer 114 of ALQ (350 Angstroms) was then deposited onto the light-emitting layer 120. Finally, a cathode 108 (2000 Angstroms) was deposited on the top of layer 114, which comprised of 10:1 Mg and Ag.

The device at 8.0 volts exhibited a current density of 20 mA/cm² and an electroluminescence efficiency of 5.0 cd/A. The color was green and peaked at 544 nm with a shoulder at 580 nm.

The invention has been described in detail with particular reference to certain preferred embodiments thereof, but it will be understood that variations and modifications can be effected within the spirit and scope of the invention.

What is claimed is:

1. An organic luminescent material having the following structure for use in organic light-emitting diodes as a single electroluminescent material or as a dopant, wherein:
$R_1$, $R_2$, $R_3$, $R_4$ are individual substituents or a group of substituents, and they may be identical or different, each substituent being individually selected from the following groups consisting of:
H, alkyl (—R), halogen (—X), aryl (—Ar), alkenyl (RCH=CH—), allyl (CH$_2$=CHCH$_2$—), cyano (NC—), isocyano (CN—), amino (H$_2$N—), tertiary amino (R$_2$N— or Ar$_1$Ar$_2$N—), amide (RCONR—), nitro (N$_2$O—), acyl (RCO—), carboxyl (—CO$_2$H), alkoxyl (RO—), alkylsulfonyl (RSO$_2$—), hydroxy (HO—) and single or fused aromatic heterocyclic rings.

2. An organic light-emitting device comprising:
(a) a substrate formed of an electrically insulating material which can be either an optically transparent materials or an opaque material;
(b) a conductive anode formed on the substrate,
(c) an organic hole transporting layer formed on the anode,
(d) an organic light-emitting layer structure which is doped with the organic luminescent material of claim 1 or just a single layer of the organic luminescent material of claim 1 and formed on the hole transporting layer;
(e) an organic electron-transporting layer formed on the light-emitting layer; and
(f) a cathode formed on the electron-transporting layer.

3. An electroluminescent device as claimed in claim 2 wherein the substrate is optically transparent and is formed from glass or plastic.

4. An electroluminescent device as claimed in claim 2 wherein the substrate is opaque and is formed from a ceramic material or a semiconductor.

5. An electroluminescent device as claimed in claim 2 wherein the conductive anode is transmissive and selected from the group consisting of a metal oxide, gallium nitride, zinc selenide, and zinc sulphide.

6. An electroluminescent device as claimed in claim 2 wherein the conductive anode is opaque and selected from the group consisting of a metal and a metallic compound having a work function greater than 4.1 eV.

7. An electroluminescent device as claimed in claim 5 wherein the metal oxide includes indium-tin oxide, aluminum- or indium-doped zinc oxide, tin oxide, magnesium-indium oxide, fluorine tin oxide, nickel-tungsten oxide, and cadmium-tin oxide.

8. An electroluminescent device as claimed in claim 6 wherein the metal is selected from the group consisting of gold, iridium, palladium, and platinum.

9. An electroluminescent device as claimed in claim 2 wherein the organic hole-transporting layer is formed of a material including hole-transporting aromatic tertiary amine molecules.

10. An electroluminescent device as claimed in claim 2 wherein the electron-transporting layer is formed of a material selected from benzazoles or the group consisting of metal chelated oxinoid compounds.

11. An electroluminescent device as claimed in claim 2 wherein the cathode material is selected to have a work function less than 4.0 eV.

12. A self-luminous display, characterized in that display is emitted from an electroluminescent element composed of a cathode, an anode, and an organic layer which contains a luminescent zone and is held between said cathode and an anode and said luminescent zone contains the luminescent material pNNA or a derivative thereof.

* * * * *